(12) United States Patent
Bilir et al.

(10) Patent No.: US 10,628,555 B1
(45) Date of Patent: Apr. 21, 2020

(54) SYSTEM AND METHODS FOR DISEASE MANAGEMENT

(71) Applicant: Collaborative Network 4 Clinical Excellence, LLC, Littleton, CO (US)

(72) Inventors: Bahri M. Bilir, Littleton, CO (US); Esra T. Nutku-Bilir, Littleton, CO (US); Mehmet Kazgan, Denver, CO (US)

(73) Assignee: Collaborative Network 4 Clinical Excellence, Inc., Denver, CO (US)

( * ) Notice: Subject to any disclaimer, the term of this patent is extended or adjusted under 35 U.S.C. 154(b) by 283 days.

(21) Appl. No.: 14/243,549

(22) Filed: Apr. 2, 2014

Related U.S. Application Data

(60) Provisional application No. 61/807,561, filed on Apr. 2, 2013.

(51) Int. Cl.
*G06F 19/00* (2018.01)
*G06Q 10/00* (2012.01)

(52) U.S. Cl.
CPC .............................. *G06F 19/3481* (2013.01)

(58) Field of Classification Search
CPC ........ G06Q 50/22; G06Q 50/24; G06Q 40/08; G06Q 10/10; G06F 19/322; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00;
(Continued)

(56) References Cited

U.S. PATENT DOCUMENTS 4,491,725 A * 1/1985 Pritchard ............... G06Q 20/10
235/378
5,583,758 A * 12/1996 McIlroy ............... G06F 19/325
705/2
(Continued)

*Primary Examiner* — Eliza A Lam
(74) *Attorney, Agent, or Firm* — Polsinelli PC

(57) ABSTRACT

A system and method for optimal disease treatment involving a disease management workflow for specific disease states, computer program products (that is, patient data repositories, workflow tools, and reports) to assist clinicians with the management of specific disease states, and the like for optimizing treatment and management of specific diseases. The system provides a workflow tool for a specific disease state that includes a pathway with decisions to be made by a clinician based on specific patient data from a repository and other patient information available to a clinician for treating a variety of medical conditions based on the up-to-date treatment information in order to provide patients with optimal treatment workflows for their specific medical conditions. A disease management pathway potentially includes parallel flows (also called "equal outcome variables") where several drugs or other treatments have been shown to have substantially equal outcomes.

13 Claims, 10 Drawing Sheets

(58) Field of Classification Search
CPC ........ G16H 40/20; G16H 40/40; G16H 40/60;
G16H 40/63; G16H 40/67; G16H 50/00;
G16H 50/20; G16H 50/30; G16H 50/50;
G16H 50/70; G16H 50/80; G16H 70/00;
G16H 70/20; G16H 70/40; G16H 70/60;
G16H 80/00
See application file for complete search history.

(56) References Cited

U.S. PATENT DOCUMENTS

| | | | | |
|---|---|---|---|---|
| 6,047,259 | A * | 4/2000 | Campbell | G06F 19/325 705/2 |
| 2002/0111826 | A1 * | 8/2002 | Potter | G06F 19/327 705/2 |
| 2007/0061393 | A1 * | 3/2007 | Moore | G06F 17/3089 709/201 |

* cited by examiner

SYSTEM AND METHODS FOR DISEASE MANAGEMENT

CROSS REFERENCE TO RELATED APPLICATIONS

This application claims priority under 35 U.S.C. § 119 from U.S. provisional application No. 61/807,561 entitled "SYSTEM AND METHODS FOR DISEASE MANAGEMENT," filed on Apr. 2, 2013, the entire contents of which are fully incorporated by reference herein for all purposes.

FIELD OF DISCLOSURE

The present disclosure generally relates to systems and methods for disease management. More specifically, the disclosure relates to systems and work flow tools including disease management pathways for optimizing management of specific diseases and decreasing overall disease management costs.

BACKGROUND

In our current medical system, patients seeking treatment for a diagnosed medical condition may undergo treatments that are inferior to the best possible and available treatment methods. Although these treatments are often based on guidelines developed by various medical societies, significant variations in the actual treatment of a patient may be observed due to lack of treatment specificity in the guidelines, variations in the interpretations of the guidelines, or lack of familiarity with the most current guidelines, among other things. Because guidelines are generally treated as a framework within which doctors are encouraged to operate and not as requirements, healthcare providers are often given significant freedom in administering treatments. While those treatments will typically fall within the broad parameters of the guidelines, the administered treatments may not be optimal or most up-to date. These variations in treatments provided by different healthcare providers often lead to significant differences in the treatment results as well as medical costs associated with the treatment or management of the diseases. This may especially be the case, when healthcare providers may use non-working, discontinued, discredited, and/or last resort therapies that result in, for example, unnecessary hospitalizations, ventilator dependencies or ICU stays.

Furthermore, a lack of standardized and/or optimized and updated treatment methods often result in a complex billing process and significant billing overhead as the collection of payments for rendered services often involves a multitude of steps. In particular, a patient undergoing a treatment under the current system may be presented with confusing forms prior to and following the treatment to ensure that healthcare providers receive appropriate compensation for the services that they rendered. For example, the patient may be initially required to sign an agreement of patient's responsibility for the payments not covered by their insurance. Following a visit at the physician's office, the patient may receive a billing statement from the office, detailing claims submitted to the insurance company. Another statement from the insurance company may subsequently provide information as to some portion of the bill that was not covered by insurance, which may be followed by another communication from the physician's office for an additional payment for the uncovered portion of the bill. Also, the patient may be faced with other bills from laboratories, hospitals and/or clinics for services provided at these various facilities.

Thus, there is a need for a system that helps ensure that patients receive up-to-date treatment for their identified medical conditions in a more structured fashion. Also, there is a need for a system that provides patients with a more realistic assessment of the treatment outcome and is capable of suggesting alternative effective treatment methods that may potentially lead to savings in treatment costs for both patients and payors. Furthermore, there is a need for a system that reduces disease management costs by simplifying the billing process and reducing the overhead billing costs.

BRIEF DESCRIPTION OF THE DRAWINGS

Exemplary embodiments are illustrated in referenced figures of the drawings. It is intended that the embodiments and figures disclosed herein are to be considered illustrative rather than limiting. The use of the same reference numerals in different drawings indicates similar or identical items.

DETAILED DESCRIPTION

Figure 1:
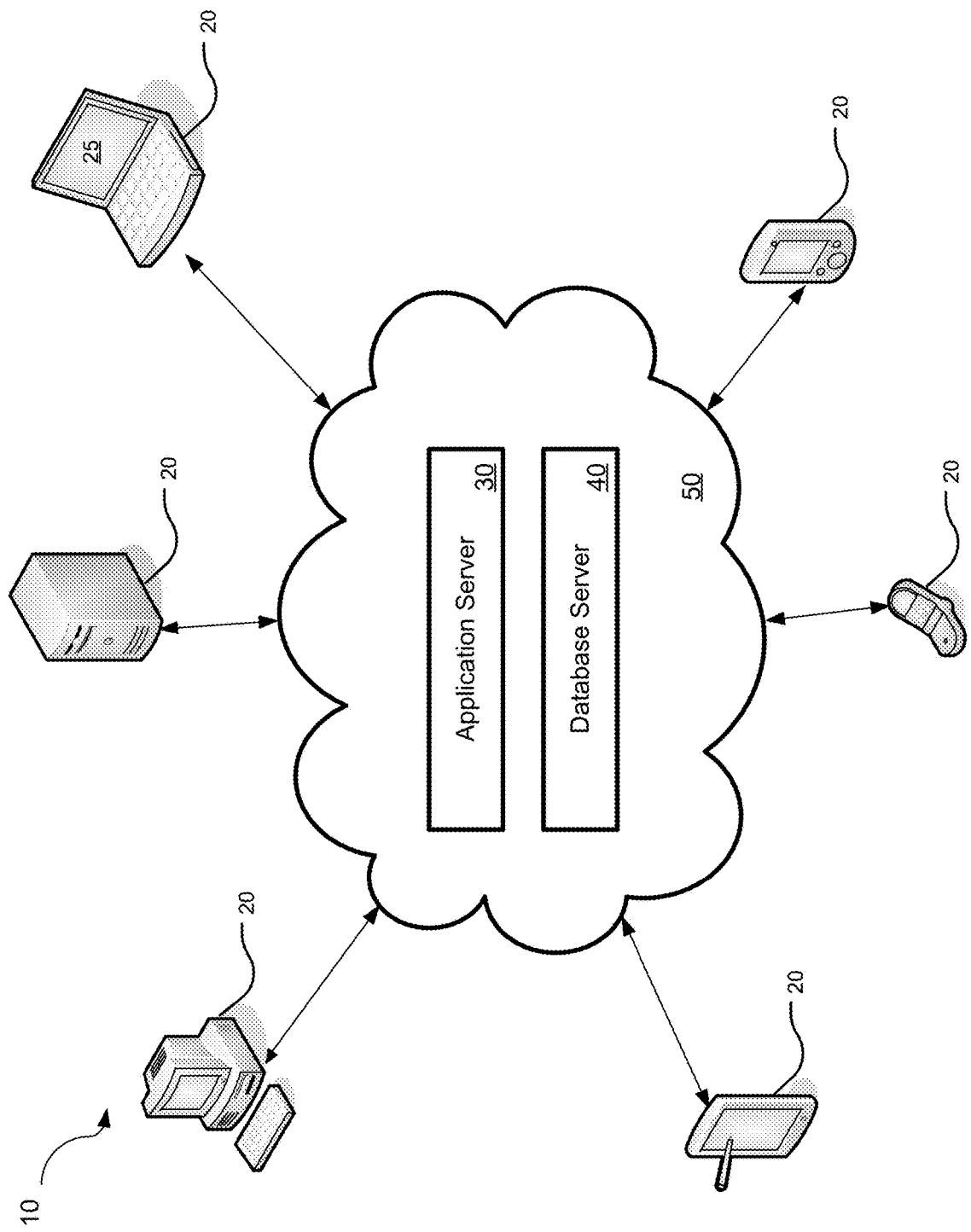
FIG. 1 is a schematic diagram illustrating an exemplary operating environment for providing an optimized disease treatment and management.

Aspects of the present disclosure involve systems, disease management pathways for specific disease states, computer program products (that is, patient data repositories, workflow tools, and reports) to assist clinicians with the management of specific disease states, and the like for optimizing treatment and management of specific diseases. In one example, the system and pathways involve the delivery of cutting edge, evidence based, disease-specific treatment workflows. In particular, the system provides a workflow tool for a specific disease state that includes a pathway with decisions to be made by a clinician based on specific patient data from a repository and other patient information available to clinician for treating a variety of medical conditions based on the up-to-date treatment information in order to provide patients with optimal treatment workflows for their specific medical conditions. A disease management pathway potentially includes parallel flows (also called "equal outcome variables") where several drugs or other treatments have been shown to have substantially equal outcomes.

The disclosed system involves a clinical excellence board (CEN-Board) which is composed of clinical excellence medical board (CEN-Medical Board), clinical excellence ethical board (CEN-Ethical Board), collaborative network for clinical excellence (CN4CE), Medical Director, and or CN4CE Scientific Director. The CEN-Medical Board is composed of physicians who have expertise in areas of disease focus. In general, they oversee all the protocols and assure the clinical structuring and implication for all treatment workflows. In particular, the medical board works with CEN-Ethical Board, CEN-physicians (CEN-P), CEN-expert panel members (CEN-EPM or also known as EPMs) to develop, review and approve the equal outcome variable (EOVs) and the workflows. More specifically, the CEN-Medical Board will: 1. act to promote an awareness of clinical issues related to treatment workflows; 2. serve as a source of recommendations and ideas for resolution of clinical problems relating the treatment workflows; 3. act to involve in the development and review of workflows and related medical society guidelines regarding clinical developments or updates or changes; 4. serve as a forum and source of expertise and recommendation for resolution of clinical conflicts in specific cases. Individual medical board members, depending on their area of expertise, may choose to act as a project manager to oversee the development, management and implementation of the disease specific treatment workflows and or may work with CN4CE's Medical Director in selection of EPMs for consensus meetings.

The disclosed system provides an ethical board as part of the clinical excellence network (CEN) which is composed of lay individuals and qualified members, who have no financial interest or involvement. In general, the CEN-Ethical Board oversees all the protocols and assures the ethical structuring and implication for all treatment workflows. In particular, ethical board oversees and works with CEN-Medical Board, CEN-P, CEN-EPM to identify, review and approve the EOVs and the workflows. More specifically, CEN-Ethical Committee will: 1. act to promote an awareness of ethical issues related to healthcare ongoing basis; 2. serve as a source of recommendations and ideas for resolution of ethical issues and conflicts within and or related to treatment workflows; 3. act to involve in the development and review of workflows and related medical society guidelines regarding ethical issues in patient care; 4. serve as a forum and source of ideas and recommendation for resolution of ethical conflicts in specific cases.

In one embodiment, the system may provide for developing and dynamically updating treatment workflows based on data and information supplied to the system by subscribers to the system. In particular, the disclosed system may serve as a tool to facilitate interactions between various subscribing members to the system, in order to initially define a treatment workflow, to record and analyze inputs concerning treatment using the defined treatment workflow, and to allow for modifications of the treatment workflow, among other functions. In general, the disease management pathway for a specific disease state is provided by a clinical excellence network (CEN) that includes healthcare professionals that have expert knowledge of the disease state, clinicians who use the system, and non-healthcare community members chosen for their high ethical standards. In particular, the system takes advantage of input from various possible participants of the CEN including clinical excellence network participating physicians (CEN-P) that participate in the development of the treatment workflow, as well treat patients using the treatment workflows, key opinion leaders (KOLs) and expert panel members (EPMs) that are experts in a certain field, experts in particular drugs, etc., but may not be treating a patient using the treatment workflows.

Expert panel members and KOLs are selected and invited to participate in CEN by a clinical excellence network board (CEN-Board). The CEN-Board involves medical board members (CEN-Medical Board), and ethical board members (CEN-Ethical Board) who are experts and professionals that can meaningfully contribute to the initial development of the treatment workflows, as well as monitor and evaluate their use, and contribute to their improvement. The system provides for developing and dynamically updating treatment workflows by a CEN when collaborative network for clinical excellence (CN4CE) when reviews new and feedback information in the system and determines that it warrants a change in a disease management pathway or equal outcome variable. Treatment workflows may be defined and revised within the disclosed system or may be developed, in whole or in part, outside the system and imported therein.

The disclosed system also provides for automated analysis of cost savings associated with complying with the provided treatment workflows. In particular, a number of data analysis tools are included for determining the cost savings achieved by payors such as participating insurance companies or medical service providers following and complying with the provided treatment workflows. More specifically, information on the reduction in both treatment and billing costs are determined and provided to the participants.

Additionally, the disclosed system may include a reward program that encourages system subscribers to utilize the system and comply with the supplied treatment workflows. In particular, the system may include tools for determining compliance with the prescribed treatment workflows and redistribution of cost savings realized through the utilization of the treatment workflows, based on predetermined number of criteria.

In general, the disclosed system is designed to provide patients with access to the latest and up-to-date treatment workflows. In particular, the system provides patients with access to treatment centers and physicians in close proximity to their homes that utilize the latest and most effective therapies otherwise only available at the most advance centers typically located at some distant location. The system also provides an infrastructure dedicated to interacting with consumers, such as insurance companies, medial facilities or physicians that allows them to provide feedback on treatment workflows based on newly acquired data and information, for review. In particular, the system includes number of modules through which up-to-date information relevant to a specific treatment may be entered and analyzed in order to arrive at most effective treatment workflows.

Referring now to FIG. 1, a schematic diagram illustrates an overview of a system 10 for providing medical treatment workflows for treating specific diseases according to the various concepts discussed herein. The system involves one or more client systems 20, which may be any form of computing device with a network connection (e.g., laptop, desktop, tablet, smart phone, terminal) running a browser or other interface 25 for accessing an application server 30. The application server may be a web server that includes a database and/or a connection to a database server 40. Communication between the client and the server may be secure and/or encrypted.

The application server 30 includes an application or applications that provide tools that help treat and manage patients with specific diseases. In particular, the application server may include an application or applications that provide for the creation, data storage, tracking, management, analysis and reporting of disease specific-treatments, among other things. Additionally, the application server may include an application that may also provide data tools for medical research. In particular, data collected using the system may serve as knowledge-base for further treatment development.

The database server(s) 40 stores data that is managed by the application(s) located on the application server. In one particular example, shown in FIGS. 2A and 2B, the database server(s) may include a treatment workflows database 40A for storing disease specific treatment workflows developed using the various processes described herein, patients database 40B for storing data related to patients undergoing treatments based on the disease specific treatment workflows, organization database 40C for storing information related to participating payors, and physicians database 40D for storing information on participating physicians.

In one particular example, the treatment workflows database 40A may store disease specific treatment workflows customized for each organization (e.g. payor) as permitted by the FDA regulations and within medical guidelines. The treatment workflows database may include a number of disease-specific treatment workflows that may be different for each individual payor. For example, the disease-specific treatment workflows that are based on medication options that have clinically and FDA proven-equal outcomes and that have been individually negotiated with and by each payor may be included in the database.

The patients database 40B may include patients demographic information such as age, sex, disease type, address, phone number, insurance type, and/or patient's history, including but not limited to patient current medical condition, response to the treatment, medical history, family history, past and current medications history, past hospitalizations, past surgery information, medication types, doses, and administration times, laboratory work-up, treatment start date and stop date, among other things.

The organization database 40C, for example, may include information about patients whose treatment costs are to be covered by the contracted payors, with each payor having an associated patient number, along with information including but not limited to patient code, physician code, insurance code and/or illness code. Additionally, the organization database may include information pertaining to agreed-upon or negotiated drugs, tests, procedures, etc. that are to be included in a payor specific treatment method. Generally speaking, a payor may provide feedback to CEN and play an active role in development and/or approval of a treatment workflow for a patient that the payor covers. In particular, a payor pays for use of the system by healthcare professionals. They negotiate a best price for an equal outcome variable (EOV) and request that CN4CE implement one or more EOV in a disease management pathway in the system used by healthcare providers (or CEN-P). Such disease management pathways or treatment workflows are developed within the context of the system with the difference that they are tailored for a specific payor. In addition, the organization database may also include standard treatment costs agreed upon per treatment that would be used as a reference for calculating cost savings. For example, the standard treatment costs may be determined from the typical treatment costs observed prior to the use of the treatment workflows developed using the system discussed herein and/or non-payor based treatment workflows. The physicians database 40D may include information such as, address, phone number, credentials, among others for all the participating physicians.

According to one embodiment, access to the information in the databases may be restricted to the members who are responsible for the development and management of the disclosed CN4CE. A limited access to the information stored in some of the databases, such as for example patients database, may be given to other subscribing system members only if deemed necessary by the CN4CE members and for a limited time only, for example, during consensus meetings scheduled for developing, reviewing and modifying treatment workflows. Generally speaking, a consensus meeting involves the collaboration of participants of CEN to define, refine or otherwise come to a consensus on a treatment workflow. Consensus meetings and more specifically how the system facilitates the same, are discussed in more detail herein. Alternatively, data could be unavailable for access until the consensus meeting in order to comply, for example, with HIPAA regulations.

In one specific implementation, both the application and the database servers may be part of a cloud computing environment 50 located at a remote location wherein the client systems 20 may access application(s) though different portals. For example, physician, organization and administrative portals may be provided for accessing the application(s) and database servers.

The application server 30 may host an application that provides users with disease management tools and disease related information. In particular, as shown in FIG. 2A, the application server (or servers) may host a website 100 that provides access to a disease management application 200 (DMA/CLIEXA) and a knowledge based application(s) 250 that provides access to the disease related information.

In one specific example, the knowledge base application(s) 250 may include a number of different modules, such as news module 250A, blogs module 250B, clinical excellence network (CEN) module 250C and a support module 250D. The news module 250A may provide access to disease related information through various news links. The CEN module 250C may provide access to the list of network (e.g. participating) physicians, information on the specific features of the network, or an online application for applying for CEN membership among other things. According to one embodiment, the CEN module may also serve as a portal through which certain members may gain access to the system for internal communications and knowledgebase access. For example, the CEN module may include information regarding time and place of a consensus meetings, office information of the participating physicians (including address, phone numbers, etc.) curriculum vitae of the participating physicians and/or physician's reviews and inputs related to disease topics.

Figure 2A:
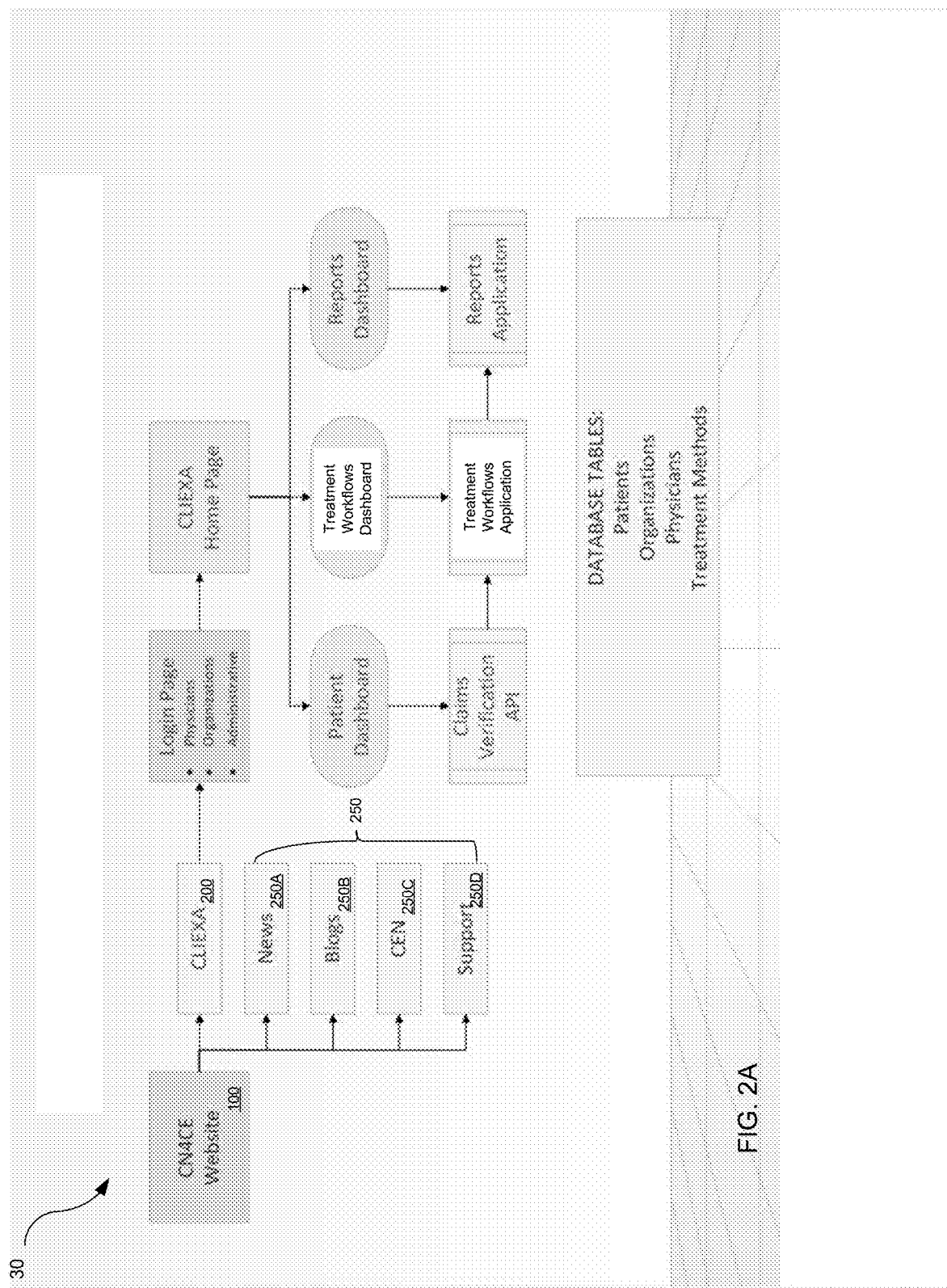
FIGS. 2A and 2B are schematic diagrams of a system designed to provide optimized disease treatment and management.
Figure 2B:
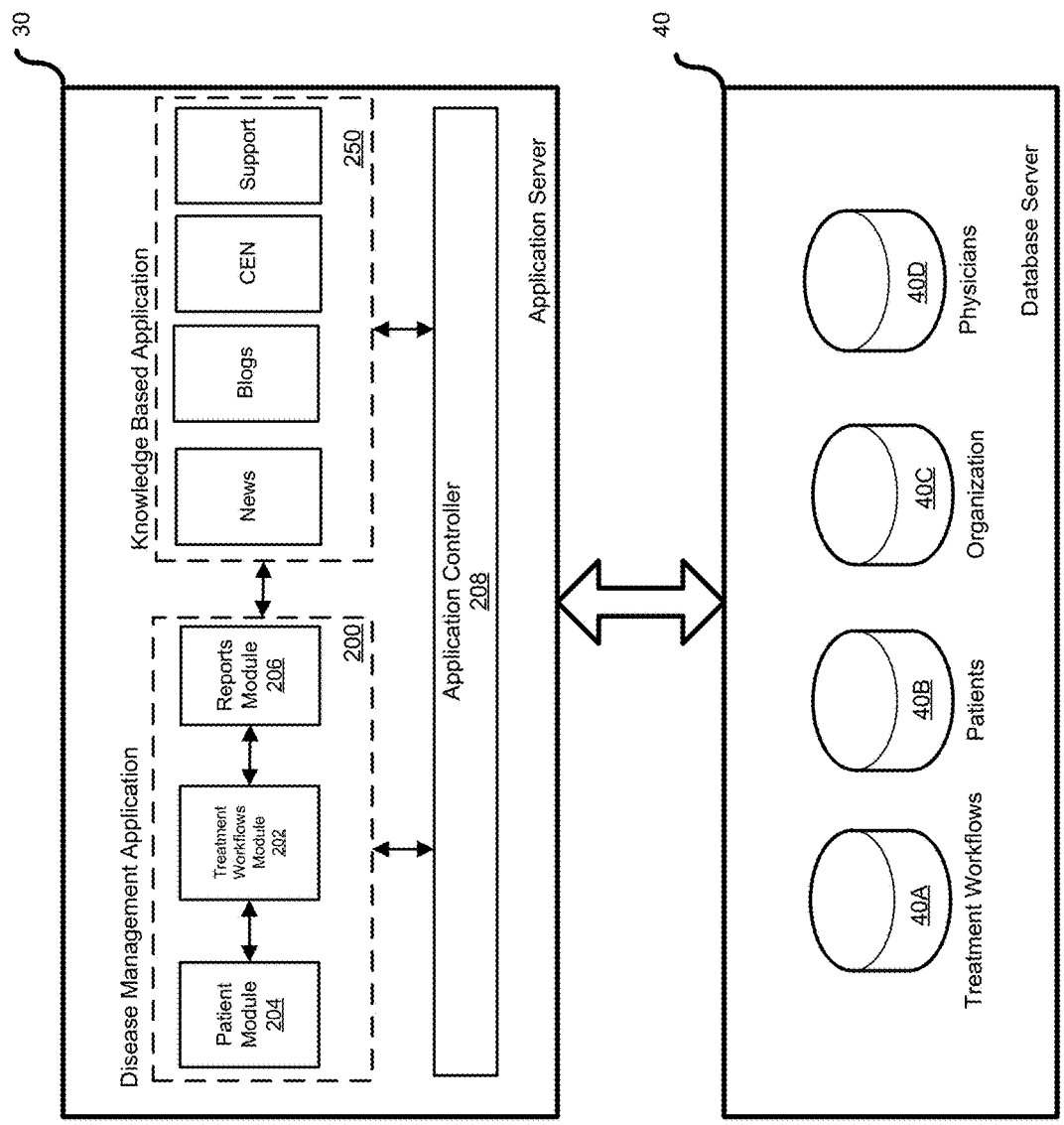

FIG. 2B provides an alternative view of some of the components and functions illustrated in FIG. 2A. Referring now to FIG. 2A as well as FIG. 2B, the DMA 200 includes number of interconnected modules that help users treat and manage specific diseases efficiently and effectively. In particular, the DMA includes such modules as a treatment workflows module 202, a patient module 204 and a reports module 206. In general, the treatment workflows module 202 is used to develop and provide access to treatment workflows for treating specific diseases. The patient module 204 provides the functionality to track, collect, store and retrieve patient related information and the reports module 206 analyzes data previously stored in any of the databases and generates reports.

According to one embodiment, access to the DMA, or at least some portions of the DMA, may be restricted to subscribers. In particular, the system may be member-specific, and password and HIPAA protected when necessary. In one example, access to the DMA may be controlled through an application controller 208 where a user name and a password, for example, entered by a subscriber may be processed and used to provide access to authorized areas of the system. Thus, for example, in order to take advantage of the information and data available through the system, entities such as payors (e.g. insurance companies), clinics, hospitals, physicians would need to first subscribe and log into the system.

In one specific example, the system may provide various subscription levels, with different features being available to the different types of subscribers. For example, clinical experts, KOLs and CEN-Ps who are part of an expert panel and thus subscribe to the system through an expert panel member (EPM) portal that may be provided through either the CEN module as discussed above or alternatively through the DMA application, may be provided with an option to review, evaluate and approve changes to treatment methods. On the other hand, a payor, such as for example an insurance company representative accessing the system through a payor/organization portal may be provided with an option to track and view current treatment methods and made aware of any new treatment workflow updates. The payor may also be provided with a view of billing information reports and given an option to approve transactions. A participating healthcare provider (e.g. CEN-P), such as a physician or physician assistant, who accesses the system through a physician portal, may be given an option to enter patient related information and select specific treatment method, as well as provide feedback regarding current treatment workflows and submit proposed changes to the treatment workflows for review by CEN-Board and EPMs. Similarly, medical and ethical board members may be given the option to access the system to participate in the implementation of the system as described 308.

According to one specific implementation, the ability to subscribe to the system may be further restricted to previously pre-approved entities. For example, participation as a CEN-P may be limited to physicians with a certain level of experience and/or expertise. Similarly, panel members may be limited to those experts with a demonstrated clinical expertise in the treatment of a certain disease.

A treatment workflow module 202 shown in FIG. 2B, also referred to as a treatment workflow application (FIG. 2A) may be accessed by any of the client systems 20 shown in FIG. 1, through, for example, a treatment workflows dashboard provided on a web page. The treatment workflow module provides the subscriber with access to any number of possible treatment workflows that may be used to treat a patient. For example, treatment workflows for treating and/or managing diseases including but not limited to the areas of gastroenterology, oncology, hepatology, cardiology, rheumatology, nephrology among many others may be provided. According to one embodiment, access to the treatment workflows 202 module as well as access to the treatment workflows dashboard through which the treatment workflows module may be limited to only certain system subscribers, such as for example, CEN-Ps.

Figure 3:
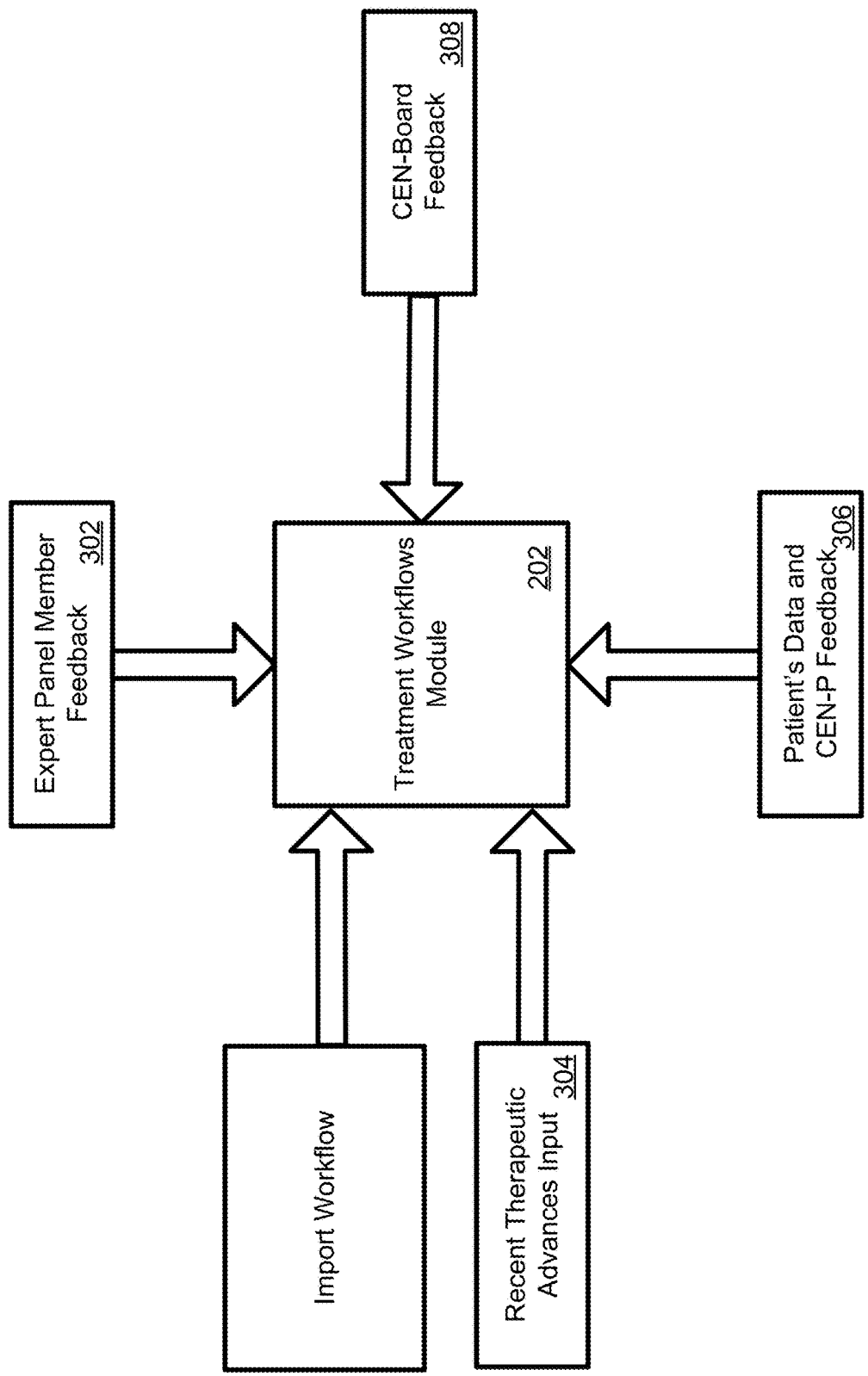
FIG. 3 is an exemplary disease management pathway (also referred to as a "treatment workflow") module included in the disclosed system.

As shown in FIG. 3, each medical treatment workflow may be designed and/or updated using information from a plurality of sources in order to arrive at an up-to-date treatment workflow for a specific medical condition. The treatment workflows as well as the computing objects used to from portions of the workflow associated with the disclosed system may be modular in nature. For example, new steps may be added, or removed, or modified if new treatment methods become available and when the new medical evidence necessitates such changes, while at the same time allowing other steps to remain unchanged. Additionally, workflow objects or steps may be employed in other treatment workflows should any two workflows have overlapping steps. Similarly, a workflow object may be generally defined such as by defining a certain treatment step involving the use of a drug at a particular dose for a particular period of time. The general object may then be tailored for a specific treatment by defining the particular drug, the particular dosage and the particular period of time for the specific treatment workflow, and then inserting that particularly defined object into the particular workflow.

Each medical treatment workflow may be developed and/or updated by CEN when the CEN-Board reviews new information receives feedback from CEN (i.e., Board, EPMs, CEN-P), and when CN4CE determines that it warrants a change in a disease management pathway or equal outcome variable through feedbacks from the system including the payor. In one specific implementation, shown in FIG. 3, each medical treatment workflow may be developed and/or updated during and/or following, for example, a mediated and scheduled scientific and clinical consensus meeting conducted by CN4CE members that are responsible and integrally involved in the development, implementation and maintenance of the system. In one specific example, the initial medical treatment workflow may be developed by using input received from experts in a given medical field, such as CEN-Board 308 and EPMs 302 and information gathered from various resources on recent therapeutic advances 304 including the newly published clinical evidence or a new and/or better FDA approved medication becomes available. Subsequently, the medical treatment workflows may be modified based on feedback and data collected and entered into the system by CEN-Ps 306 on patients undergoing treatments following the initially developed treatment workflows, as well as any other feedback received from experts 302 or newly identified information on recent therapeutic advances 304. More specifically, the treatment workflows module may receive feedback information, collect, assemble and analyze data from any of the above identified sources in order to alert the system to develop and provide a knowledge-base for a review on an optimal and up-to-date evidence based treatment method for a given disease. In other words, the treatment workflows module gathers newly collected and/or provided information related to the treatment of a specific disease in order to alert the system to determine the need for change in the treatment.

In one particular example, information on the most recent advances in a specific medical area may be collected from medical journals or governmental sources, while adhering to established medical society guidelines. In particular, the system may query and identify relevant information located within these sources either automatically or individually collected or entered into the system. Furthermore, patient related data which may include such information as patient's current condition, response to the treatment, drug doses, among other things, as well as CEN-P observations and feedback on the effectiveness of the treatment may be collected by accessing systems that are dedicated to collecting specific type of information. Thus, for example, laboratory results may be obtained by accessing a system located in a laboratory performing prescribed tests, CEN-P's observations may be obtained by accessing a system located in CEN-P's office and any data collected at a facility where a patient underwent treatment may be obtained by accessing the facility's systems. Any information identified and collected by either the EPMs and or the CEN-Board as relevant to the currently administered treatment workflows, as well as their opinions based on such information may be entered as feedback information into the system for a further review through the EPM portal and or CEN-Board Portal, respectively. Either the EPMs or CEN-Board members, for example, may be provided with options to enter information into the system via a text editor or fill in provided predefined fields, among other things.

According to one embodiment, the feedback information may include a recommendation to stop a treatment or modify one of the initially defined or created treatment "stop points" or "study end points." In general the "stop points" or "study end points" within a treatment workflow are used to indicate non-working, last resort therapies or points within the treatment workflow where a particular illness is observed as no longer benefiting from any therapeutic measures after a certain point. In particular, the "stop points" are located at a branch in the treatment workflow where a certain set of previously conducted treatments have resulted or arrived at a point where no other treatment options are available or the treatment has been successful. Also, the "stop points" may be converted into additional steps or options when new and/or breakthrough findings arise during the implementation of specific treatment.

According to one embodiment, each time new information, data, or feedback is entered into the treatment workflows module, a notification or alert can be generated and sent, for example, to each EPM and or CEN-Board member for evaluation based on number of pre-selected criteria, as well as CN4CE management who would be directly and primarily responsible for arranging consensus meetings involving CEN, reviews of treatment workflows and renewals by the EPMs. For example, CEN-P provided feedback on irregular results and created alternative workflows and paths for treatment workflows may generate a notification or alert that may be subsequently provided for review and approval by the EPMs and CEN-Board. The notification or alert trigger points, may be initially defined and stored in the system when a new treatment method is developed, and can be subsequently modified based on the need.

In response to the received notification, alert or at a predefined point in time, a consensus meeting occurs where the panel of experts (e.g. EPMs) and the CEN-Board may review and evaluate any newly collected and/or provided information and makes a recommendation, approve, update and/or otherwise change or define a treatment workflow to reflect the most recent findings. To achieve this, the system may provide an interface, such as, for example, a chat module, interactive web conferencing module, or any similar infrastructure that would enable geographically dispersed members of the panel of experts to gather and discuss the newly discovered data or information. Furthermore, the system may provide the ability to update any of the treatment workflows upon reaching a consensus. For example, the system may provide a number of predefined text fields for accepting text input describing the agreed upon changes or updates to the treatment. The system may also include number of interactive objects that once selected would enable the users, EPMs, CEN-Board members or otherwise assigned users, to receive feedbacks to review.

Figure 5:
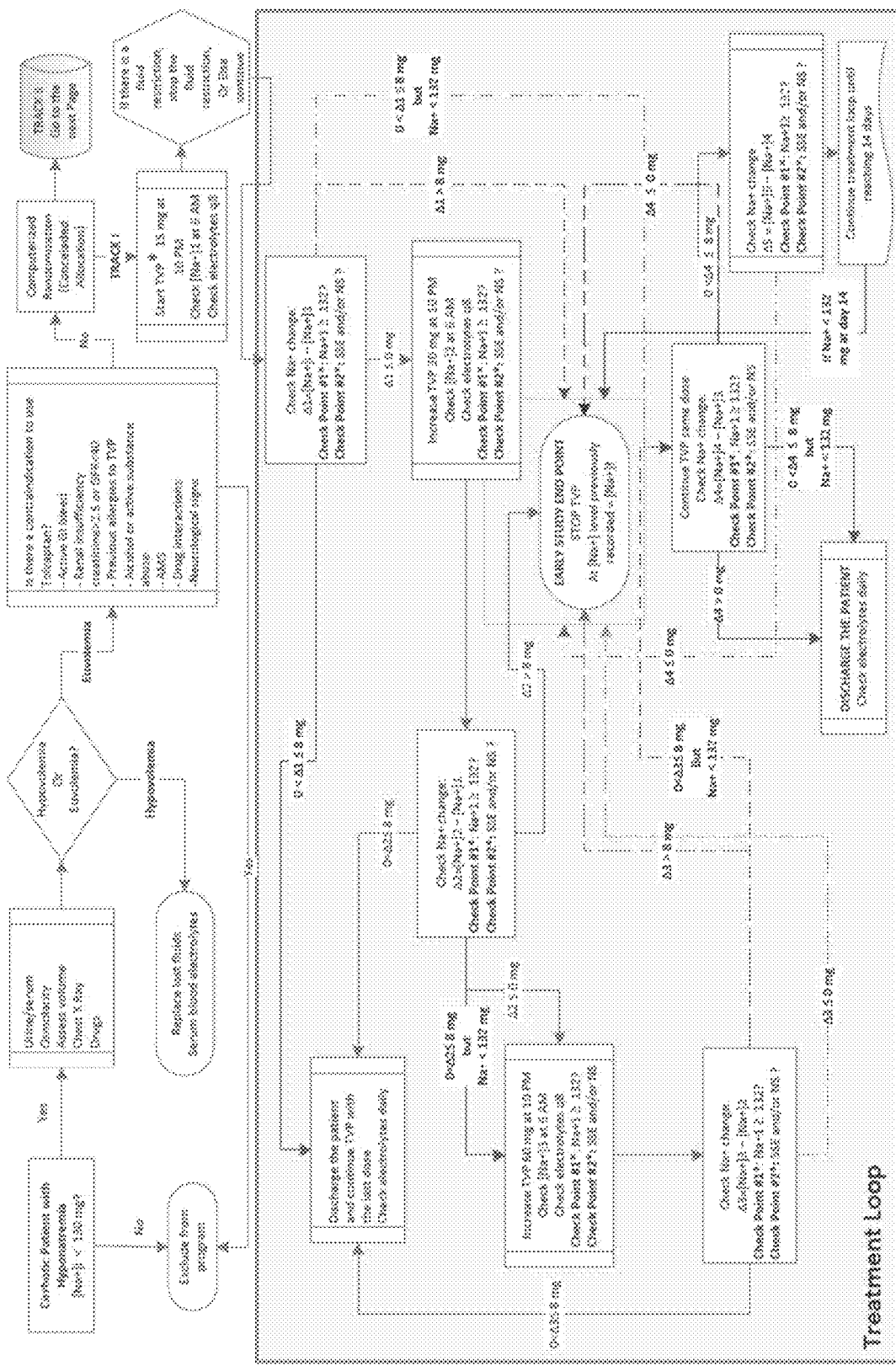
FIGS. 5 and 6 show an exemplary disease management pathway that can be generated by disclosed system to treat a specific disease.
Figure 6:
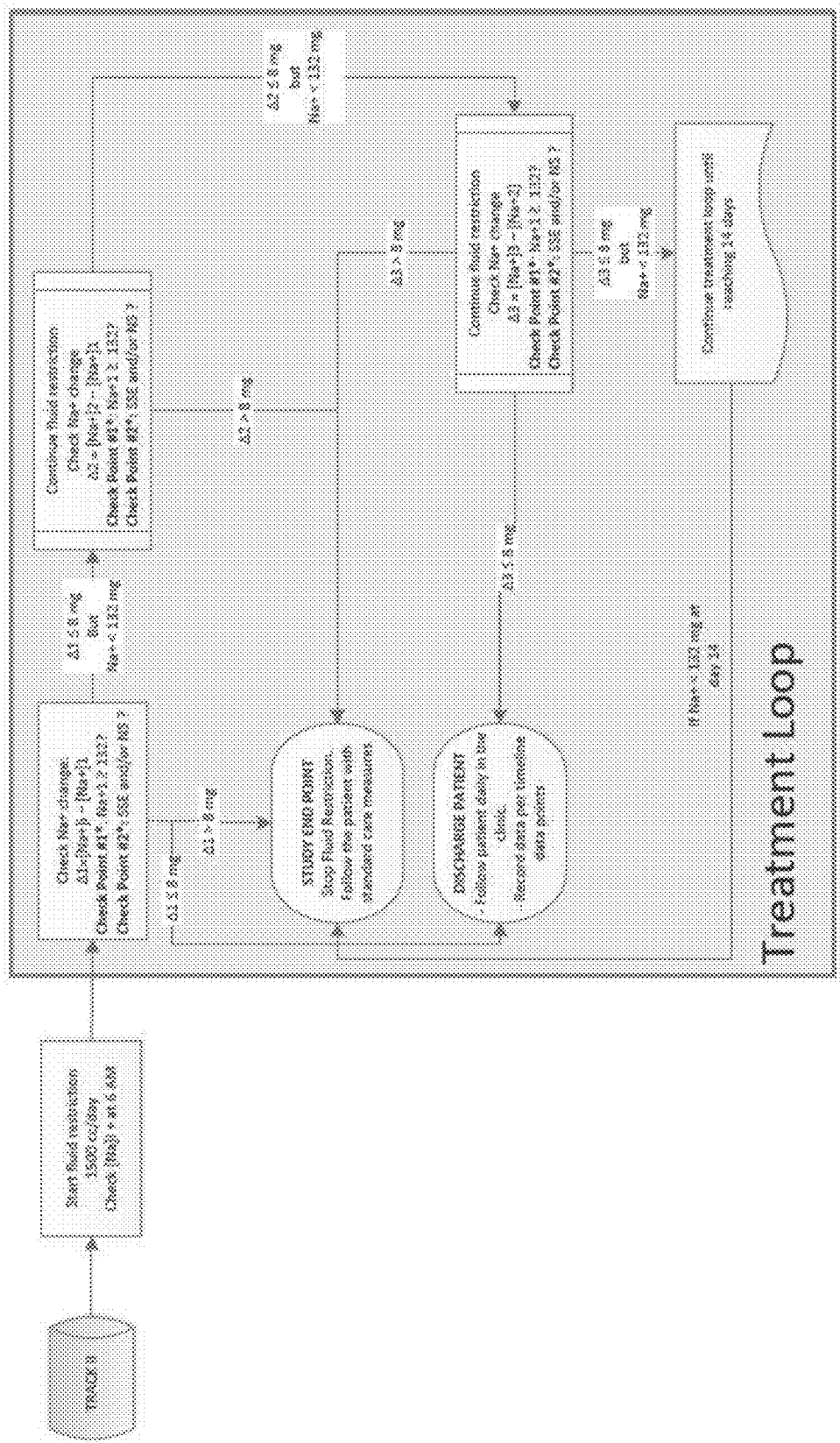

FIGS. 5 and 6 show an exemplary treatment workflow that can be utilized by CEN participating physicians to treat hyponatremia resulting from liver cirrhosis. In particular, a treatment workflow for treating patients with hyponatremia, using a drug, such as for example, Tolvaptan™ (Track I) or using fluid restriction (Track II) is shown in FIGS. 5 and 6, respectively. As shown, both tracks in this treatment workflow provide CEN-Ps with specific treatment options and check points that can be used to evaluate effectiveness of the treatment and provide needed feedback.

In general, a treatment workflow shown in the figures includes and defines a number of check points that may be used to determine discharge and admission points, need for emergency room visits, and treatment "stop points," among other things. In particular, as shown in the figures the defined checkpoints may be provided as interactive objects that may be used to determine the next treatment step within the treatment workflow. For example, when using a laboratory result value as a checkpoint measure, such as for example change in sodium (Na) levels shown in FIG. 5, the treatment steps may be determined based on a pre-defined criteria or threshold against which the received patient data and information may be compared in order to arrive at the next step within the treatment workflow. Thus, for example, as shown in FIG. 5, upon a selection of an object that allows determining a change in patient's Na+ level, the next recommended treatment step may be based on the observed Na+ level change (e.g. $\Delta 3$). More specifically, a change in Na+ value of greater than 8 mg may lead to an early study end point, wherein a change of less than 8 mg may suggest continuing the treatment by administering a previously administered drug dose. The use of various checkpoints and study end points as indicated herein plays an important role in, for example, decreasing the length of hospital stay, readmission and emergency visits and eliminate the need for unnecessary second opinions, reducing prolonged hospitalization, ventilator dependency or ICU stay or other unnecessary care.

In addition to collecting data, the system also provides a subscriber with the ability to record, track and report and or validate outcomes of each patient's treatment workflow. In general, outcomes are the metrics, which determine the progression of a treatment workflow. These metrics can involve various measures involved in the treatment workflows and are disease-specific. For example, length of hospital stay, duration of a specific treatment, number of usage of a certain type of a medication, any laboratory values before, during and after a certain treatment and or medication, number of hospital and or clinical visits, number of a certain therapy and or injection received or specific procedures done, number of admissions or re-admissions before and after the treatment and or medication are some of the metrics that the disclosed system uses in order to validate the outcomes. Validation is done by gathering the related data from the databases. Disease-specific patient satisfaction surveys may also performed as outcome validation as part of the patient module.

Figure 4:
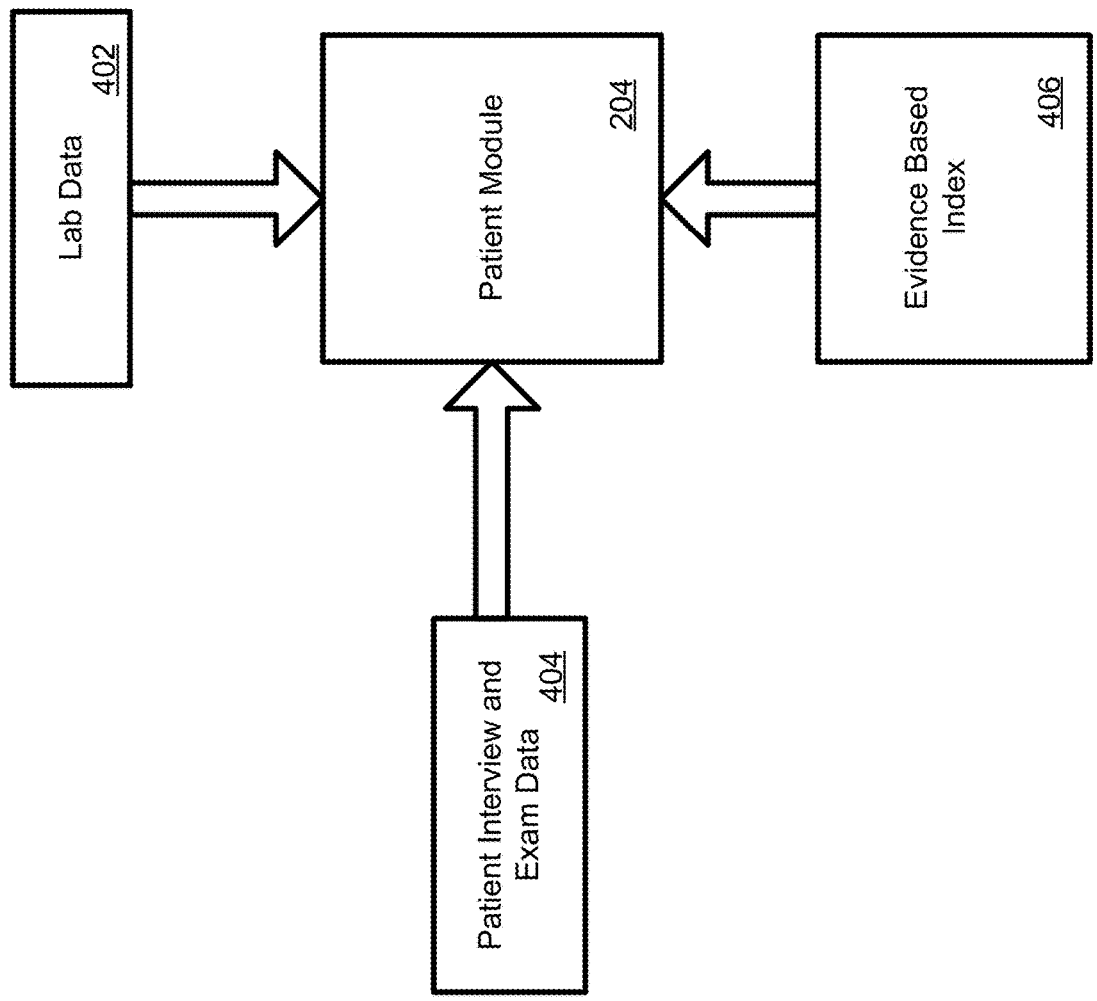
FIG. 4 is an exemplary patient module included in the disclosed system.

The patient module 204, shown in FIGS. 2B and 4, which may be accessed through, for example, a patient dashboard shown in FIG. 2A, provides subscribers with an instant and step by step tracking of visits and treatments for patients that consent to participate in treatments according on one of the disease specific treatment workflows. In particular, the patient module records, tracks and manages patient related information that is stored in the patients database. The patient related information may be collected during examination or during an interview with the patient (e.g., during a phone conference with the patient while the patient is being treated or afterward) and may be entered into the system through a provided user interface by a CEN-P treating the patient in accordance with one of the system's treatment workflows. Additionally, data corresponding to medication type, doses and time of administration, results, collected during a hospital stay, may be accessed and retrieved by the patient module from a hospital database, and managed through the patient module. Generally speaking, the patient module may be used to collect and track data related to a patient's condition, progress, response to and/or completion of treatment, patient compliance with the treatment, and patient-specific outcome validation with the relevant information being entered into the system through the patient module by a subscribing CEN-P or by accessing and retrieving patient information from other databases.

As shown in FIG. 4, historical data in the database related to the specific disease will be indexed and can be used to provide statistical data along with the other treatments as a reference when related. This module in the system called "Evidence Based Data Index" (EBDI) will be enabled throughout the treatment and displays statistical data using historical evidence (e.g., "N number out of M patients had shown X type of complication at this stage" where N equals the number of patients from historical data that have a similar type of treatment applied with similar symptoms, and M equals the number of patients with the similar treatment applied throughout the database.)

In addition to collecting patient related data, the patient module may provide the subscriber with an ability to initiate insurance verification process or to automatically generate, verify and submit medical claim forms for the provided treatment to a payor, such as insurance company or any other organization that may be involved in covering treatment costs. In particular, when a new patient is added to the system, patient insurance information is updated and/or treatment is to be started or continued (e.g. the patient is about to enter next phase or step of the treatment), the patient module may verify the insured status of the patient in order to ensure that treatments that are to be administered are covered by the payor. For example, an application programming interface (API) may be provided that compares patient insurance data with the payors database to verify that the patient is still insured and eligible for the continuation in the treatment program. Claim verification may further involve verifying compliance by the CEN-P with the patient treatment workflow. Also, the patient module may provide payors with an ability to provide incentives to the patients, such as waving of deductibles and/or out of pocket expenses, to encourage patient compliance with the provided treatment workflows. Overall, various possible implementations of the system may encourage, monitor, and otherwise facilitate both patient and physician compliance.

Additionally, the information provided and entered into the system by the CEN-Ps during each patient visit, step or phase of the treatment may be used to automatically generate and submit medical claims to the payors. In one specific example, the information collected through the patient module may be sent to the reports module that in response generates and submits billing information to the appropriate payors. According to one embodiment, the billing reports may be submitted via an email or appropriate API. The automated billing process is in part possible due to the fact that the payors are closely involved in the development of the treatment workflow thereby eliminating the need for following some of the steps involved in a typical billing process. In other words, the automation of the billing process substantially reduces the pre-approval, billing, collection and any other overhead costs at both the physicians and health insurance company levels thereby providing substantial cost savings to the healthcare providers and other parties involved.

The patient module, upon completion of the insurance verification process and in response to the collected patient data, also provides access to a disease specific treatment(s) that may be selected and retrieved from the treatment workflows database. In particular, the patient module may suggest the most appropriate treatment workflow(s) for a given patient based on the collected information. For example, a treatment workflow corresponding to the particular needs of a patient may be provided to the CEN-P that is based on the entered patient laboratory results and insurance information to ensure that the patient is provided with the most effective and payor approved treatment options.

Furthermore, the patient module may analyze collected information and use the results to help update the treatment specific workflows. In particular, information on the response of a patient to a prescribed treatment workflow may be used to determine effectiveness of the prescribed therapy and or individual patient outcome validation or a need to alter or update the disease-specific treatment workflow with the current medical treatment information in order to optimize the treatment. For example, the patient related data and information may be compared to predicted treatment outcome defined at various treatment check points within the treatment workflow and any irregularities or significant variations from the specified outcome may be used to alert CEN-Ps, CEN-Board and the EPMs and CEN-Board of the effectiveness of the treatment and or need for treatment modification.

In one specific implementation, the patient module may be setup to automatically detect irregularities and variations between the patient's response to the treatment and the predicted treatment outcomes defined in the treatment workflow. In particular, the patient module may compare any newly entered patient data to the information stored within the treatment workflow to determine if any of the expected treatment outcomes have been reached in response to the provided treatment or if the actual treatment outcome differs from any of the expected treatment outcomes. For example, referring now back to FIG. 5, if a determination is made that an early study end point has occurred in response to the 43 value being equal to 7 mg instead of the expected 8 mg, an irregularity would be noted by the system for the given treatment workflow.

Alternatively, the patient module may allow the treating CEN-P to enter comments or suggestions to modify treatment workflow based on the CEN-Ps observations and/or identified irregularities and variations. Regardless of the method for identifying irregularities or variations, the system may generate an alert and send notifications to the EPMs and CEN-Board involved with the development of the specific treatment workflow indicating the detected irregularities or variations and/or comments or suggestions entered by the CEN-P. In one specific example, the alert may be in a form of an e-mail, a text message or a visible icon (!) on the EMPs and or CEN-Board's dashboard. According to one embodiment, the alert along with the patient data and information on the identified and noted irregularities or variations may be also sent to the treatment methods module for further analysis and consideration where it may be initially reviewed by a selected CN4CE member, such as for example, a CN4CE scientific director and or a CEN-board member. Depending on the type of the alert, a consensus conference may be arranged by the CN4CE scientific director in order to review the reason for the alert in more detail. In particular, the consensus conference may be used to determine the severity of the issue that generated the alert, additional value provided by the suggestions, or existence of a common problem in the treatment workflow that would necessitate a change to the current treatment workflow.

Furthermore, information collected and recorded at the various stages of treatment, may also be used by the system to assess, for example, CEN-P's compliance with a treatment protocol. In general, compliance can take on several forms. For example, since the treatment workflow is not meant to replace the judgment of an experience physician, a deviation from the treatment workflow may be observed when a physician changes treatment steps based on his/her experience. Although, technically the physician may not be compliant with the system through such action, the patient may nonetheless be provided with appropriate treatment. Another form of non-compliance may involve the CEN-P failure to enter the required information into the system so that the progress and compliance with the treatment workflow cannot be accurately tracked.

According to one embodiment, a compliance-tracking function may be provided in the patient module that may be used to determine a level or percentage of compliance with the treatment workflows by a specific CEN-P. The compliance-tracking function may, for example, compare the information entered by the CEN-P to requirements specified within the treatment workflow. Thus, for example, when a treatment workflow is provided to the CEN-P in a series of steps, execution of each step would determine if the treatment protocol is being sufficiently followed. In such instance, the CEN-P may be required to enter required information that would indicate that a particular step of the prescribed treatment was executed and thus compliant with the treatment protocol achieved. The information determine by the compliance-tracking function may be later used by the reports module to determine rewards to be distributed to physicians as discussed below.

The disclosed system also provides tools for generating reports on both the effectiveness of the treatments provided according to the developed treatment workflows, as well as billings and cost savings achieved through their use. As shown in FIGS. 2A and 2B, reports may be generated by accessing a reports module or reports application through, for example, a reports dashboard. In particular, the reports module may provide billings for the provided treatment and cost savings summary on the measured and track total savings based on number of different parameters.

According to one embodiment, the reports module may automatically generate billing reports for patient undergoing treatments using one of the provided treatment workflows. In particular, as discussed above, the system provides a simplified method for generating billing reports by having a participating patient automatically pre-approved and covered for the visits and medical expenses associated with the treatment.

The reports module may also provide for determining cost savings achieved based on the parameter(s) set, for example, for a particular illness with a specific payor. In particular, the system may use objective quantifiable variable for determining cost savings. For example, the system may calculate and provide cost savings based on the a predefined set of equal outcome variables (EOVs) for each treatment protocol, such as for example, the use of equivalent but less expensive medication, saving realized from decreased hospital stay or stop points to stop the care in order to avoid unnecessary ICU stay. The total cost savings may be, calculated using a computer implemented workflow for a specific illness based on the various EOVs used. Alternatively, a cost saving for each EOV may be reported separately.

The reports module also may generate a reward summary report. In particular, the reports module may include a reward calculation function that can be used to determine, for example, financial reward to be distributed to the system participating physicians and/or other system participants. The reports module may provide the outcome of the reward calculations in the reward summary report. For example, the report summary may outline the amount of financial rewards distributed based on such variables as the number of patients treated using the provided treatment workflows, percent compliance with the treatment workflows, area of service, percent of patients treated using the treatment workflows versus another choice of treatment, or total cost savings realized, among other things may be generated. The reports module, also may generate an outcome validation report. In particular, the reports module may include an outcome validation calculation function based on pre-determined treatment workflow-specific metrics as outcomes and patient satisfaction survey results. Thus, for example, the number of steps executed by the CEN-P in accordance with the protocol (workflow) is used to determine the metrics and whether or not the treatment and results were appropriate and successful. Similarly, patient satisfaction surveys may contain responses available in a form of frequencies, distribution and or grading (numbers and or points) for each question, where the questions relate to any number of possible issues associated with a particular treatment step, use of a drug and EOV, and the like. The greater number of metrics and or patient survey points, specific to each treatment workflow, would lead to a greater and better outcome validation points being calculated. Outcome validation can be used to determine, for example, the success of the treatment workflow for the involved patient and or overall patient groups that are treated using the system.

In one specific example, the reward summary report may include summary of compliance based reward based on the compliance information discussed above. In particular, the information determined by the compliance-tracking function provided in the patient module may be used by the reports module to determine reward to be distributed to CEN—P based on his/her compliance with the prescribed treatments. In other words, the level of a reward to be awarded may be correlated with the treatment compliance level. Thus, for example, when the number of steps executed by the CEN-P in accordance with the protocol is used to determine the compliance level, the greater number of steps would lead to a greater reward being awarded to the complying healthcare provider. The reward system is thus designed to provide incentives to the healthcare providers to utilize the disease specific treatment workflows.

In one specific implementation, the compliance-based reward system may be designed such that the reward payments may be weighted using for example, a compliance coefficient, that depends on the medical field in which the treatment is provided, illness being treated, individual patient outcome validation, geographic area in which the treatment is conducted, etc. In particular, the compliance coefficient may be dynamically modified or adjusted up or down from a baseline based on these variables in order to maximize compliance levels. For example, if the physician is in an area where complying with the treatment workflow is more difficult or in a remote area with fewer patients, the compliance coefficient maybe adjusted upwardly to encourage compliance with the treatment workflow.

Additionally, the rewards summary report may also provide a summary of rewards based on the overall cost savings achieved. In particular, the cost savings rewards may be determined from a total reward received from a payor for the realized overall cost savings with each reward awarded by the payor being based on individual contracts with each payor.

Figure 7:
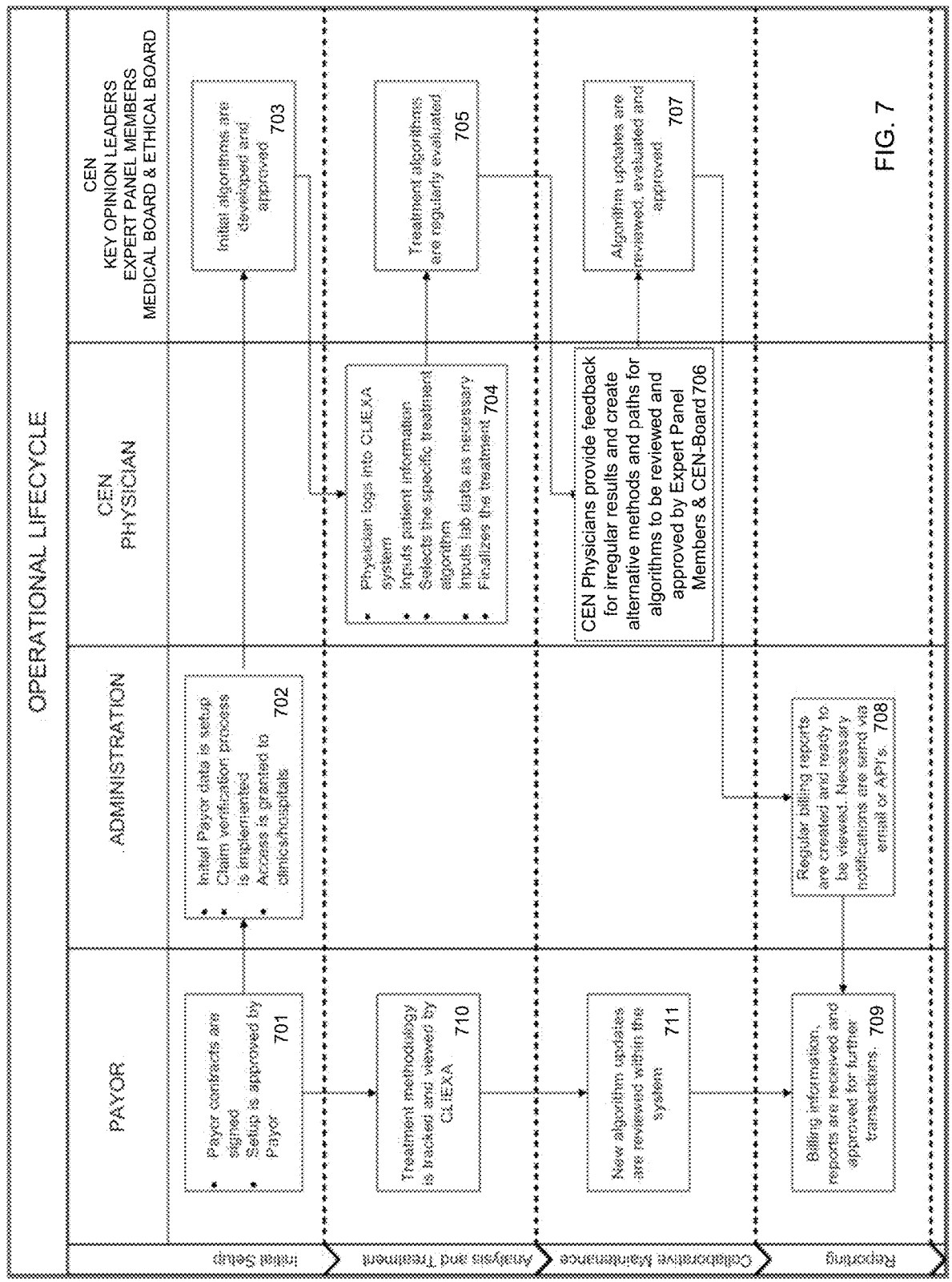
FIG. 7 are flow diagrams of processes that provide an optimal disease management at a significant cost saving according to various embodiments.

An exemplary flow diagram of the process that provides an optimal disease management at a significant cost saving according to one embodiment of the current disclosure is shown in FIG. 7. Generally speaking, the system involves action and interaction by various subscribers to the system during four phases of initial set-up, analysis and treatment, collaborative maintenance and reporting. As shown in the FIG. 7, the disease management process begins with a payor, such as for example a health insurance company, subscribing to the system and approving development of a treatment workflow (step 701). The subscription to the system may involve, for example, signing of a contract and agreeing to certain terms and conditions associated with utilizing the system. Following the initial agreement signing, payor data may be collected and stored in the system for future use. For example, system may store information for claim verification process or patient insurance status verification process (step 702). Also, access to the system may be granted to subscribing clinics, hospitals, or other interested parties at this time.

Referring still to FIG. 7, an initial treatment workflow may be first developed and approved at the initial setup phase by CEN-Board and the EPMs that includes clinical experts, KOLs and or CEN-Ps for each specific disease (step 703). To achieve this, the system provides a user interface, communication medium and functionality for CEN-Board and the EPMs to propose a treatment workflow, comment on the treatment workflow, and eventually approve the treatment workflow. In one implementation, the system may provide a meeting scheduling function that allows a CN4CE member and CEN-Medical Board to schedule a consensus meeting for the purpose of developing, and at a later time modifying a treatment workflow or conducting other work related to the treatment workflow. Also, the system may provide the medium by which the geographically remote team members may conduct a consensus meeting.

Once the initial treatment workflow is approved, during the analysis and treatment phase, a healthcare provider, such as CEN-P, may access and use the treatment workflow to treat patients (step 704). The CEN-P may begin accessing and using the treatment workflow after initially logging into the system. Because the treatment workflow selection is based on the patient's needs, the CEN-P may first enter patient related information into the system prior to selecting or being provided with a specific treatment workflow. The system, thus, may additionally allow the CEN-P or related approved staff member to enter laboratory data or any other patient related information as needed, to further aid in the treatment selection process.

In one particular example, the treatment workflow may involve a collection and arrangement of interactive computing objects that are associated with one or more steps in the treatment workflow whereby a treating CEN-P may interact with each object, the collection of which provide the CEN-P with a disease specific treatment workflow for a given patient. Thus, for example, a user interface is provided whereby the physician may enter initial patient data and may select an initial treatment workflow. Where appropriate, the physician may interact with unique objects of the treatment workflow to obtain specific treatment information. For example, if the treatment workflow is associated with use of a specific drug, a dosing object may be included in the treatment workflow whereby the physician enters in patient data and the object produces an output corresponding with the proper dosage and time of the dosage. Additionally, the CEN-P may be provided with a "black box warnings," such as for example, side effects or life threatening risks, as well as drug interactions with the particular drug(s) that are being used within the treatment workflow or any other possible negative outcomes related to using the drug(s) specified by the treatment workflow. Similarly, CEN-P may also be provided with a list of disease-specific patient inclusion and exclusion criteria that are being used within the treatment workflow.

When a patient enters the final stage of the treatment, or needs to be excluded based on disease-specific treatment workflow exclusion criteria and/or develops a disease-specific treatment workflow exclusion criteria after being involved in the workflow, the CEN-P may be provided with an object that provides information on why the treatment is being finalized and allow the CEN-P to take the patient out of the treatment. In particular, since each treatment workflow has a final outcome, such as for example, the patient is cured, laboratory values are normalized or a "stop point" after which no available treatment would give any objective benefit to the patient and outcome, among others, once one of the outcomes is reached the CEN-P may be allowed to close and file the particular treatment workflow for the patient. Once the specific treatment method is closed the patient may continue to be cared for by the CEN-P and/or enrolled into a different treatment workflow if new options leading to new treatment workflows arise or new issues arise in the course of their disease treatment. Thus, for example, a patient with a hepatitis C virus (HCV) may be off the treatment workflow as a non-responder to the antiviral treatment but if they develop cirrhosis afterwards may be enrolled in the liver transplantation treatment workflow.

The system further provides an interface by which CEN-Board and the EPMs may track and evaluate treatment using the treatment workflow (step 705) at regularly scheduled intervals. In one specific example, as discussed above, CEN-Board and the EPMs may log into the system to evaluate a treatment workflow, through the provided CEN module and after being granted access to the system by, for example, a CN4CE member in response to an alert. Once logged into the system, CEN-Board and the EPMs may be provided with data for their evaluation in various forms including patient specific windows displaying some or all patient data, dosages, timing, etc., and such data or patient information may also be provided in other forms, such as through graphs and charts.

The effectiveness of treatment based on the treatment workflow may also be evaluated albeit not changed, by the CEN-Ps administering treatments to patients. The CEN-Ps may provide feedback on any irregular treatment results in response to the treatment and suggest alternative workflows and paths (step 706) by interacting with the system through a provided user interface. In one particular example, the feedback, observations and/or suggestions for alternative workflows and paths may be provided by entering text messages into the system that may be at a later time reviewed by the EPMs, CEN-Board and CN4CE scientific director.

Depending on the implementation, in response to the provided feedback and or suggestions to treatment modifications, an alert may be generated by the system to ensure that the provided information is promptly reviewed, evaluated and approved (step 707). Thus, for example, any changes to the treatment workflow suggested by the CEN-Ps may be forwarded to the EPMs, CEN Board and CN4CE scientific director, for example, through an email or may be made available for retrieval though the system interface once a notification or alert is sent. The suggested changes and/or modifications along with appropriate feedback may be reviewed by the EPMs, CEN-Board and CN4CE scientific director and if a consensus is reached a recommendation may be made to modify or change the treatment workflow.

According to one embodiment, prior to the actual change or modification of the treatment workflow, the recommendation to modify or change treatment workflow approved by the EPMs CEN-Board and CN4CE scientific director may be first forwarded to the payor(s) for review and/or approval (step 708). This may be done by sending a notification to the payor that a new version of the treatment workflow is ready and posted to production. Generally speaking, each payor is made aware of and given an opportunity to review and approve the treatment workflow, and the proper use of the approved treatment workflow in order to ensure that the subsequently submitted bills are later approved. Furthermore, through both the analysis and treatment phase as well as during a collaborative maintenance phase of the process, payors are provided access to track and view a treatment methodology (step 710) and review any new treatment workflow updates (step 711). This review and approval process is implemented to ensure that the payor specific-disease-specific treatment method is based on the latest negotiated and payor selected EOVs. Also, because some of the recommended therapies may costs thousands of dollars, the payors involvement in the approval process may be needed to ensure that the prescribed therapies are appropriately reimbursed once implemented and under certain circumstances, to strike a balance between providing alternative treatment steps with proven effectiveness and the treatment cost.

As the treatment workflow continues to be used to provide treatment in its current, updated version by the CEN-Ps, each time the system is accessed billing reports may be automatically generated based on the patient information collected during the patient visit (step 708). According to one embodiment, the billing reports may be viewed prior to being submitted to the payor to ensure their correctness. Thus, for example, in one specific implementation, the system may respond to an input indicating the end of a patient visit by generating a billing report. The system may extract information needed to generate the billing report from the information provided by the treating physician and display the report for review to ensure accuracy and correctness of the information. If an inaccuracy is detected in the billing report, the system may allow for manual entries to the billing report prior to the bill submittal.

The submitted billing information may subsequently be received by the payor and approved for further transactions (step 709). The billing report may be accessed by the payor either through a provided system interface or the billing report may be directly sent to the payor. The received billing reports may be customized based on the payor selected criteria, such as number of patients, etc. for evaluation purposes. Thus, the system provides flexibility based on the payor's preferences and/or the infrastructure used.

Figure 8:
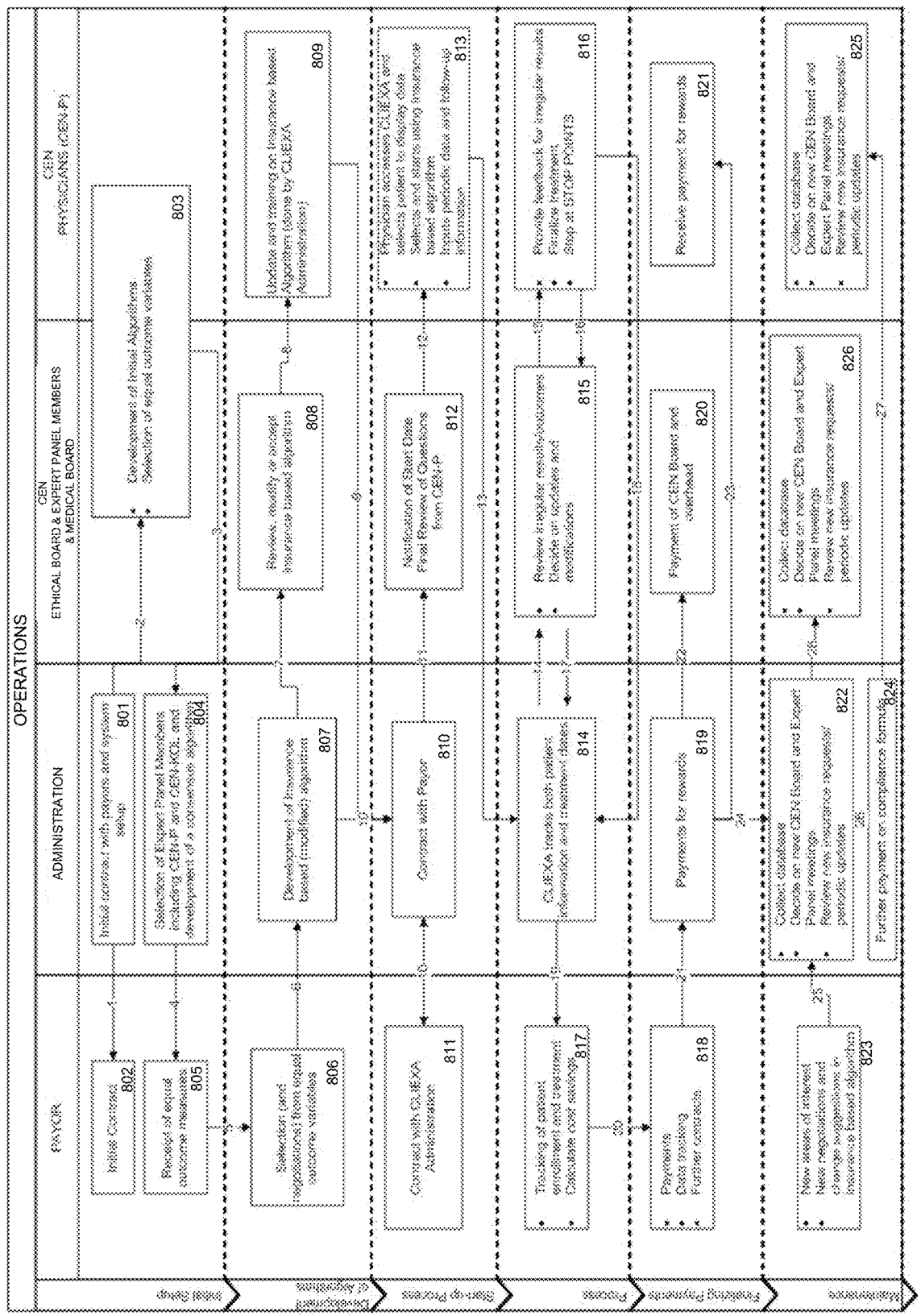
FIG. 8 is a flow diagram of a process that provides an optimal disease management at a significant cost saving according to another embodiment.

Shown in FIG. 8 is a flow diagram of a process that provides an optimal disease management at a significant cost saving according to a different embodiment of the current disclosure. As shown in FIG. 8, the process involves action and interaction between payors, administrators, the EPMs, CEN-Board (CEN-Medical Board and the Ethical Board) and CEN-Ps during six different phases of initial set-up, treatment workflow development, start-up process, treatment and analysis process, payment finalizing and maintenance. During the initial setup phase the process may begin with the system administration setting up the system and generating initial contracts for distribution to selected payors (step 801). The initial contracts may include an initial agreement by the payor to participate in the development of the treatment workflows. By accessing the system, the system administration (e.g. CN4CE board members) may be provided with an option to select and/or generate appropriate contracts and distribute the contracts to selected payors.

In response, the selected payors may accept terms and conditions listed in the initial contract (step 802) at which point development of initial treatment workflow and selection of equal outcome variables (EOVs) that could lead to potential treatment cost savings may begin (step 803). As shown in FIG. 8, the treatment workflow development and selection of EOVs may be done through a collaborative effort among the EPMs compatible with current disease treatment guidelines and the most recent applicable scientific data, and when needed under the supervision and guidance of, for example, a CN4CE medical director and CEN-Board during consensus meetings. For example, the EPMs may identify medications, tests and/or procedures that provide equal therapeutic value or a surgical versus non-surgical management of an illness or in-patient versus out-patient management of illness. The defined EOVs may be provided to the payors for their review and approval. To facilitate development process, the system may provide a medium by which the team may meet to establish the treatment workflow. In one example, the system may provide an interface to facilitate virtual meetings, such as a chat module, interactive web conferencing module, or any similar infrastructure.

Once the initial treatment workflow(s) is/are developed and the EOVs are selected, the system administrators (e.g. CN4CE members) and CEN-Medical Board may begin a selection process of the CEN-P and the EPMs that would be involved in a more in depth treatment workflow development (step 804). The CEN participants (e.g., CEN-P, the EPMs, CEN-Board) may also at this time develop a consensus method to be followed during the treatment workflow development process. The system may, for example, provide an interface through which the CEN participants may enter specific criteria that would need to be met in order to change or modify an existing treatment workflow. For instance, the system may implement an interactive voting process that would allow the team members to vote on any proposed change or modification or a rating process that would allow to evaluate the criticality of the proposed change or modification implantation into the treatment workflow. The list of selected EOVs, along with both the list of the EPMs, as well as the treatment workflow, may be subsequently sent to the payors (step 805).

The payor and/or payors may review the submitted information and select EOVs of most interest to the payor(s) (step 806). The payor may also be able to suggest and/or negotiate EOVs that were not previously considered with the CEN participants to have the variables included in the treatment workflow. Once appropriate EOVs are selected and/or negotiated, development of the payor approved, disease specific treatment workflows may begin (step 807). In other words, the initially developed treatment workflow may be appropriately modified to reflect the input provided by the payor.

The developed insurance based treatment workflow may be submitted to the CEN-Board and the EPMs for review and approval (step 808). When appropriate, the proposed insurance based treatment workflows may be further modified by the CEN-Board and the EPMs before being accepted and released to the CEN-Ps as one of the available treatment workflows. As shown in FIG. 8, prior to the use of any newly developed or updated treatment workflow, the system may provide appropriate training to selected CEN-Ps (step 809). In one example, the system may provide a training module, through which the participating physician may be provided with an overview of the treatment workflow and its features, as well as information on its use.

In order to take advantage of the data collected via the system, the payor or any other party interested in such information may either contract or subscribe to the system. Thus, for example, a payor may contract with the CN4CE system administrators (step 811) by agreeing to system terms and conditions as specified by the system administrators (step 810). A notification on the availability of treatment workflow may be sent to interested, subscribing/contracting parties along with a request for any questions or feedback related to the treatment workflow (step 812). Once all the raised issues and/or questions are addressed the updated treatment workflow is made available for use to the system subscribers. In one particular example, the participating CEN physicians may begin using the system after an initial login that may be physician specific and HIPAA compliant (step 813). The CEN-P may access the available treatment workflow, which is now specific to the payor preferred EOVs through a user interface and begin interacting with a number of computing objects associated with one or more steps in the treatment workflow to obtain specific treatment information in a similar manner as disclosed above with reference to step 704. The system may also allow the CEN-Ps to access patient data stored and/or otherwise available through the system, as well as input into the system newly collected patient information. In particular, data on the patient's response to the treatment, follow-up information, among other information, may be entered for later use and/or reevaluation of the proposed treatment workflow through a provided interface.

Referring still to FIG. 8, during treatment administration process in accordance with the developed treatment workflow, the system may continually track both patient information and treatment dates as provided by participating CEN-Ps (step 814). In one particular example, the collected data may be stored in a provided patient database and be later made available to the payor and/or other system users for review. Thus, for example, the collected and stored data may be reviewed by CEN-Board and the EPMs in order to identify irregular results/outcomes and to decide if any updates or modifications to the treatment workflow are needed (step 818). Also, the stored data may either be sent to or accessed through a provided user interface by a payor to track patient enrollment and treatment and to calculate the cost savings realized through the system (step 817).

In addition to tracking and storing patient data, the system may provide the CEN-Ps with an option to provide feedback on irregular results and suggest alternate strategies, to finalize treatments or stop at predefined "stop points" (step 816). If needed and in response to the information supplied by the CEN-Ps the CEN-Board (CEN-Ethical Board and CEN-Medical Board) and Expert Panel may conduct review of the results/outcomes and make recommendations to update or modify treatment workflows (step 815) which may be then sent along with the patient information to the contracted payors for a review and or approval.

As shown in FIG. 8, a portion of calculated cost savings realized by the payor may be shared with the CN4CE system administrators (step 819) who may then redistribute the received payments through an implemented rewards system to both the CEN Board and the EPM (step 820) as well as the participating CEN-Ps (step 821).

In order to ensure that most up-to-date treatment workflows are available for number of different diseases the system is further design to be periodically evaluated and updated (step 822, 826 and 825) to reflect the needs of patients and payors. For example, the system may be updated to generate new treatment workflows in the areas of interest, as suggested by the payors (step 823), with the development of each newly requested treatment workflow being done following process steps described herein. The maintenance will also allow to extend the process to be adopted and utilized in different regions of the country or the world and or in complex illnesses in different disciplines.

Figure 9:
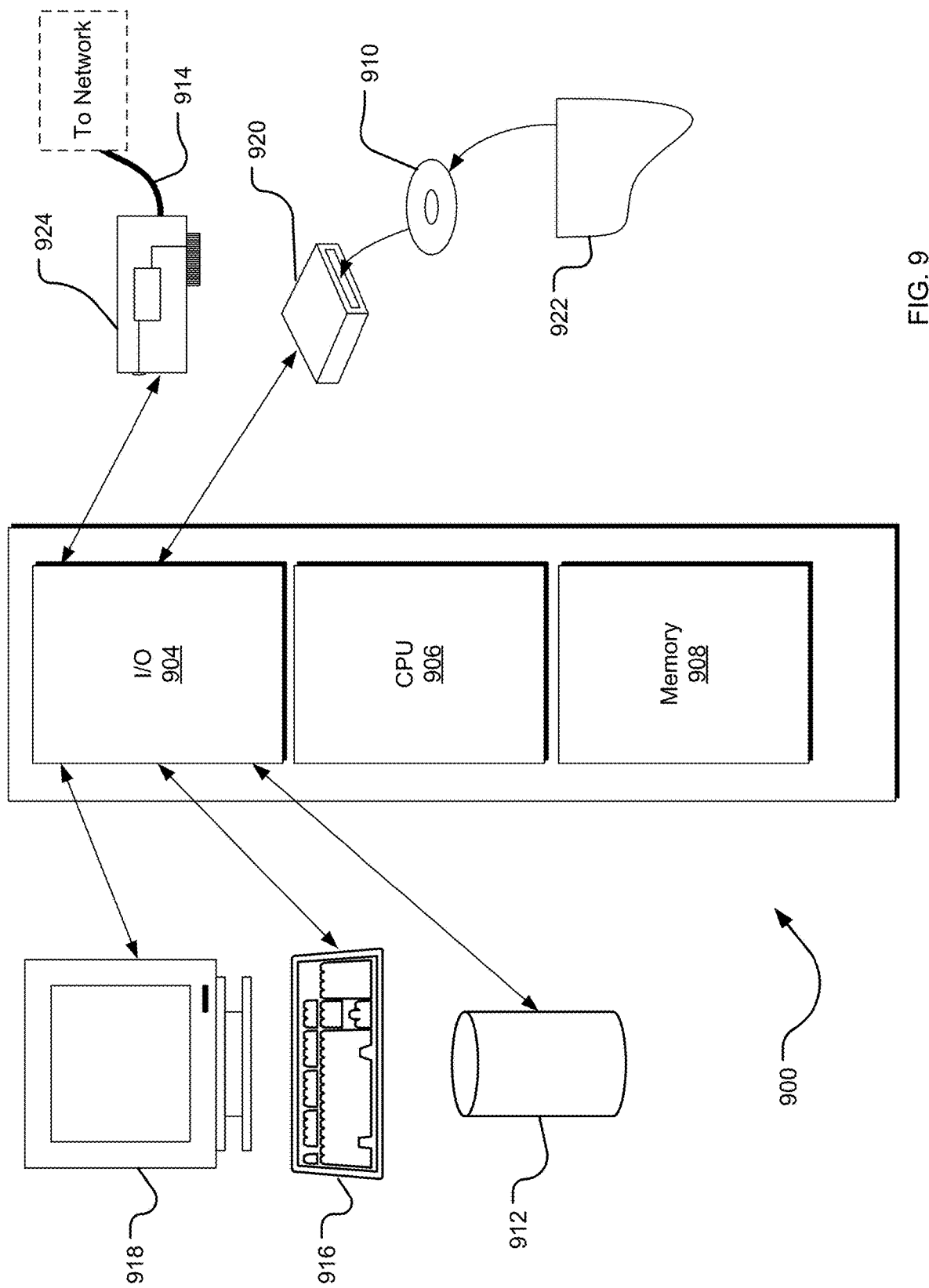
FIG. 9 is an example of a computing system that may implement various systems and methods discussed herein.

Referring to FIG. 9, a detailed description of an example computing system 900 that may implement various systems and workflows discussed herein is provided. A general purpose computer system 900 is capable of executing a computer program product to execute a computer process. Data and program files may be input to the computer system 900, which reads the files and executes the programs therein. Some of the elements of a general purpose computer system 900 are shown in FIG. 9 wherein a processor 902 is shown having an input/output (I/O) section 904, a Central Processing Unit (CPU) 906, and a memory section 908. There may be one or more processors 902, such that the processor 902 of the computer system 900 comprises a single central-processing unit 906, or a plurality of processing units, commonly referred to as a parallel processing environment. The computer system 900 may be a conventional computer, a distributed computer, or any other type of computer, such as one or more external computers made available via a cloud computing architecture. The presently described technology is optionally implemented in software devices loaded in memory 908, stored on a configured DVD/CD-ROM 910 or storage unit 912, and/or communicated via a wired or wireless network link 914, thereby transforming the computer system 900 in FIG. 9 to a special purpose machine for implementing the described operations.

The I/O section 904 is connected to one or more user-interface devices (e.g., a keyboard 916 and a display unit 918), a disc storage unit 912, and a disc drive unit 920. Generally, the disc drive unit 920 is a DVD/CD-ROM drive unit capable of reading the DVD/CD-ROM medium 910, which typically contains programs and data 922. Computer program products containing mechanisms to effectuate the systems and methods in accordance with the presently described technology may reside in the memory section 908, on a disc storage unit 912, on the DVD/CD-ROM medium 910 of the computer system 900, or on external storage devices made available via a cloud computing architecture with such computer program products, including one or more database management products, web server products, application server products, and/or other additional software components. Alternatively, a disc drive unit 920 may be replaced or supplemented by a floppy drive unit, a tape drive unit, or other storage medium drive unit. The network adapter 924 is capable of connecting the computer system 900 to a network via the network link 914, through which the computer system can receive instructions and data. Examples of such systems include personal computers, Intel or PowerPC-based computing systems, AMD-based computing systems and other systems running a Windows-based, a UNIX-based, or other operating system. It should be understood that computing systems may also embody devices such as Personal Digital Assistants (PDAs), mobile phones, tablets or slates, multimedia consoles, gaming consoles, set top boxes, etc.

When used in a LAN-networking environment, the computer system 900 is connected (by wired connection or wirelessly) to a local network through the network interface or adapter 924, which is one type of communications device. When used in a WAN-networking environment, the computer system 900 typically includes a modem, a network adapter, or any other type of communications device for establishing communications over the wide area network. In a networked environment, program modules depicted relative to the computer system 900 or portions thereof, may be stored in a remote memory storage device. It is appreciated that the network connections shown are examples of communications devices for and other means of establishing a communications link between the computers may be used.

In an example implementation, manifest file subsets and corresponding content segments, a plurality of internal and external databases, source databases, and/or cached data on servers are stored as the memory 908 or other storage systems, such as the disk storage unit 912 or the DVD/CD-ROM medium 910, and/or other external storage devices made available and accessible via a network architecture. Content streaming, distribution, and delivery software and other modules and services may be embodied by instructions stored on such storage systems and executed by the processor 902.

Some or all of the operations described herein may be performed by the processor 902. Further, local computing systems, remote data sources and/or services, and other associated logic represent firmware, hardware, and/or software may be configured to control operations of the cloud computing environment 50, the user devices 20, and/or other components. Such services may be implemented using a general purpose computer and specialized software (such as a server executing service software), a special purpose computing system and specialized software (such as a mobile device or network appliance executing service software), or other computing configurations. In addition, one or more functionalities disclosed herein may be generated by the processor 902 and a user may interact with a Graphical User Interface (GUI) using one or more user-interface devices (e.g., the keyboard 916, the display unit 918) with some of the data in use directly coming from online sources and data stores. The system set forth in FIG. 9 is but one possible example of a computer system that may employ or be configured in accordance with aspects of the present disclosure.

In the present disclosure, the workflows (or pathways) disclosed may be implemented as sets of instructions or software readable by a device. Further, it is understood that the specific order or hierarchy of steps in the workflows disclosed are instances of example approaches. Based upon design preferences, it is understood that the specific order or hierarchy of steps in the workflow can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a machine-readable medium having stored thereon instructions, which may be used to program a computer system (or other electronic devices) to perform a process and or implement systems and computing modules according to the present disclosure. A machine-readable medium includes any mechanism for storing information in a form (e.g., software, processing application) readable by a machine (e.g., a computer). The machine-readable medium may include, but is not limited to, magnetic storage medium (e.g., floppy diskette), optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic instructions.

The description above includes example systems, workflows (pathways), techniques, instruction sequences, and/or computer program products that embody techniques of the present disclosure. However, it is understood that the described disclosure may be practiced without these specific details.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

The invention claimed is:

1. A method for refining data driven workflows comprising:

using at least one computing device in communication with at least one non-transitory-storage media including computer executable instructions, the at least one computing device defining an application server that is in communication with a plurality of devices via a communication network, each device of the plurality of devices located at a remote location different from the application server, the computer executable instructions executed by the at least one computing device to perform a method of:

accessing, by at least one processor of the at least one computing device, a first treatment workflow associated with a disease data structure having historical treatment data and treatment results for a particular disease stored in a database that is provided by a database server, the first treatment workflow defining a plurality of treatment steps each defined by a respective plurality of interactive computing objects stored in the database and interconnected through pointers, the plurality of interactive computing objects including a first interactive computing object including a first patient data field that receives input via a user interface from one of the plurality of devices via the communication network, the first patient data field associated with a first threshold, the first interactive computing object pointing to a second interactive computing object including an equal outcome variable with an associated second threshold and a second patient data field that receives input from the user interface from one of the plurality of devices via the communication network, the equal outcome variable defining a first treatment option that has an equal outcome of treatment success as compared to a second treatment option not included in the second interactive computing object, the second interactive computing object pointing to a third interactive computing object reached when a second patient data value is received in the second patient data field and exceeds a second threshold and defining at least one end point reached when the second patient data value in the second patient data field exceeds the second threshold;

executing, by the at least one processor of the at least one computing device, the first interactive computing object upon receipt of a first patient data value of the first patient data field to determine if the first patient data value exceeds the first threshold;

automatically transmitting, by the at least one processor of the at least one computing device, an electronic notification directed to the plurality of devices, each device of the plurality of devices receiving particular information associated with the electronic notification having security restrictions and a user subscription level for the user of each the plurality of devices when the first patient data value exceeds the first threshold; and indexing, by the at least one processor of the at least one computing device, the historical treatment data and the treatment results, the historical treatment data and the treatment results including information from at least the first patient data field and the second patient data field, the historical treatment data and the treatment results stored in the database for the particular disease and determining an evidence based data index (EBDI) for the first treatment workflow based on the indexing of the historical treatment data and the treatment results for the particular disease, and further based on the EBDI, determining that N number of M patients had a complication based on the historical treatment data and the treatment results, and dynamically generating an improved second treatment workflow associated with the disease data structure within the database upon receiving a change to the first interactive computing object that is generated in response to the complication thereby automatically generating an additional and changed first interactive computing object, the second improved treatment workflow including the respective plurality of interactive computing objects stored in the database and interconnected through pointers with the first interactive computing object replaced by the additional and changed first interactive computing object.

2. The method of claim 1 further comprising:
in response to the first patient data value exceeding the first threshold, automatically generating a user interface including a modifiable field for generating the additional and changed first interactive computing object based on the first interactive computing object, the user interface further configured to receive at least two inputs to generate the second treatment workflow based on a consensus of a plurality of members.

3. The method of claim 2 further comprising:
upon generation of the second treatment workflow, providing access to the second treatment workflow through a user interface providing at least one selectable field to approve, reject, or request a change to the second treatment workflow.

4. The method of claim 1 further comprising:
wherein at least the second interactive computing object includes a compliance attribute linked to the second patient data field, associating a level of compliance with the treatment workflow based on a value for the second patient data field and the compliance attribute.

5. A computing system for refining data driven workflows comprising:
at least one computing device including a non-transitory media for storing computer executable instructions and at least one processor, the computer executable instructions implementing a plurality of computing modules executed by the at least one processor to:

provide access to a first treatment workflow associated with a disease data structure having historical treatment data and treatment results for a particular disease stored in a database, the first treatment workflow comprising a plurality of treatment steps between an initiation of treatment and at least one end point, the treatment steps each defined by a respective plurality of interactive computing objects stored in the database and interconnected through pointers, the plurality of interactive computing objects including a first interactive computing object including a first patient data field that receives input via a user interface from one of the plurality of devices via a communication network and a first threshold, the first interactive computing object pointing to a second interactive computing object including an equal outcome variable with an associated second threshold and a second patient data field, the equal outcome variable defining a first treatment option that has an equal outcome of treatment success as compared to a second treatment option not included in the second interactive computing object, the second interactive computing object pointing to a third interactive computing object reached when a second patient data value is received in the second patient data field and exceeds a second threshold and defining the at least one end point reached when the second patient data value in the second patient data field exceeds the second threshold;

execute the first interactive computing object upon receipt of a first patient data value of the first patient data field to determine if the first patient data value exceeds the first threshold;

automatically transmit an electronic notification directed to a plurality of devices when the first patient data value exceeds the first threshold;

index the historical treatment data and the treatment results, the historical treatment data and the treatment results including information from at least the first patient data field and the second patient data field, the historical treatment data and the treatment results stored in the database for the particular disease and determining an evidence based data index (EBDI) for the first treatment workflow based on the historical treatment data and the treatment results for the particular disease, and further based on the EBDI, determining that N number of M patients had a complication based on the historical treatment data and the treatment results; and dynamically generate a second treatment workflow within the database based on the EBDI, the complication, and upon receiving a change to the first interactive computing object, the second treatment workflow including the respective plurality of interactive computing objects stored in the database and interconnected through pointers with the first interactive computing object replaced by a changed first interactive computing object.

6. The computing system of claim 5 wherein one of the plurality of computing modules executed by the at least one processor electronically generates and electronically transmits an invoice based on the execution of the first interactive computing object.

7. The computing system of claim 5 wherein one of the plurality of computing modules executed by the at least one processor, in response to the first patient data value exceeding the first threshold, automatically generates a user interface including a modifiable field for generating the changed first interactive computing object based on the first interactive computing object, the user interface further configured to receive at least two inputs to generate the second treatment workflow based on a consensus of a plurality of members.

8. The computing system of claim 5 wherein one of the plurality of computing modules executed by the at least one processor, upon generation of the second treatment workflow, provides access to the second treatment workflow and through a user interface, the user interface providing at least one selectable field to approve, reject, or request a change to the second treatment workflow.

9. The computing system of claim 5 wherein at least the second interactive computing object includes a compliance attribute linked to the second patient data field, and wherein one of the plurality of computing modules executed by the at least one processor associates a level of compliance with the first treatment workflow based on a comparison of a value for the second patient data field and the compliance attribute.

10. The method of claim 1 further comprising providing access to an evidence based data index providing for display of statistical information concerning at least one of the plurality of treatment steps, the statistical information including historical treatment of patients in accordance with the treatment steps.

11. The method of claim 1 further comprising providing access to one or more reports addressing at least one of patient treatment based on the first treatment workflow, patient treatment metrics associated with the treatment workflow, billing information reports related to treatment in accordance with a workflow, effectiveness of treatments associated with the treatment workflow, cost saving based on treatment in accordance with the equal outcome variable, and rewards based on cost savings from treatment in accordance with the treatment workflow.

12. The method of claim 1 further comprising comparing one or more metrics entered in association with one of the plurality of treatment steps, and compare the one or more metrics to one or more respective validation metrics to generate an outcome validation.

13. A method for generating a data driven workflow comprising:
using at least one computing device in communication with at least one non-transitory-storage media including computer executable instructions, the at least one computing device defining an application server that is in communication with a plurality of devices via a communication network, each device of the plurality of devices located at a remote location different from the application server, the computer executable instructions executed by the at least one computing device to perform a method of:
accessing, by at least one processor of the at least one computing device, a first treatment workflow associated with a disease data structure having historical treatment data and treatment results for a particular disease stored in a database that is provided by a database server, the first treatment workflow defining a plurality of treatment steps each defined by a respective plurality of interactive computing objects stored in the database and interconnected through pointers, the plurality of interactive computing objects including a first interactive computing object including a first patient data field that receives input via a user interface from one of the plurality of devices via the communication network, the first patient data field associated with a first threshold and an alert trigger activated when the first threshold is exceeded, the first interactive computing object pointing to a second interactive computing object including an associated second threshold and a second patient data field, the second interactive computing object pointing to a third interactive computing object reached when a second patient data value is received in the second patient data field and exceeds a second threshold and defining at least one end point reached when the second patient data value in the second patient data field exceeds the second threshold;
executing, by the at least one processor of the at least one computing device, the first interactive computing object upon receipt of a first patient data value of the first patient data field to determine if the first patient data value exceeds the first threshold;
automatically transmitting, by the at least one processor of the at least one computing device, an electronic notification directed to at least one of the plurality of devices, the device receiving particular information associated with the electronic notification having security restrictions and a user subscription level for a user of the at least one of the plurality of devices when the first patient data value exceeds the first threshold;
in response to the alert trigger in the first interactive computing object being activated, generating, by the at least one processor of the at least one computing device, a user interface for at least one of the plurality of devices, the user interface including a modifiable field for generating a modified first interactive computing object based on the first interactive computing object;
indexing, by the at least one processor of the at least one computing device, the historical treatment data and the treatment results based the historical treatment data and the treatment results stored in the database for the particular disease and generating an evidence based data index (EBDI) for the first treatment workflow based on the indexing of the historical treatment data and the treatment results for the particular disease, and further based on the EBDI, determining that N number of M patients had a complication based on the historical treatment data and the treatment results; and
dynamically generating, by the at least one processor of the at least one computing device, a second treatment workflow within the database based on the EBDI and the complication, and upon receiving the modified first interactive computing object, the second treatment workflow including the modified first interactive computing object pointing to the second interactive computing object, the second interactive computing object pointing to the third interactive computing object.

\* \* \* \* \*